United States Patent [19]

Beauchaine

[11] Patent Number: 5,153,675
[45] Date of Patent: Oct. 6, 1992

[54] MODULAR OPTICAL SYSTEM FOR FOURIER TRANSFORM INFRARED SPECTROMETER

[75] Inventor: Kenn A. Beauchaine, Madison, Wis.

[73] Assignee: Nicolet Instrument Corporation, Madison, Wis.

[21] Appl. No.: 484,221

[22] Filed: Feb. 22, 1990

[51] Int. Cl.⁵ .................... G01B 9/02; G01N 21/01
[52] U.S. Cl. .................... 356/346; 356/244; 250/339
[58] Field of Search .......... 356/244, 346, 345; 250/339

[56] References Cited

U.S. PATENT DOCUMENTS

| | | | |
|---|---|---|---|
| 3,806,259 | 4/1974 | Boomstrom et al. | 356/244 |
| 4,120,592 | 10/1978 | Fleming et al. | 356/201 |
| 4,640,617 | 2/1987 | Hughes et al. | 356/346 |
| 4,657,390 | 4/1987 | Doyle | 356/346 |
| 4,799,001 | 1/1989 | Burch | 318/640 |
| 4,810,092 | 3/1989 | Avth | 356/244 |
| 4,847,878 | 7/1989 | Badeau | 377/19 |

FOREIGN PATENT DOCUMENTS

63-148146  6/1988  Japan ................... 356/244

OTHER PUBLICATIONS

Wilks Scientific Corporation Data Sheet, Nov. 5, 1968.

*Primary Examiner*—Davis L. Willis
*Assistant Examiner*—K. P. Hantis
*Attorney, Agent, or Firm*—Foley & Lardner

[57] ABSTRACT

A modular optical system for a Fourier transform infrared spectrometer which has a baseplate assembly with a baseplate having a top surface and two mirrors mounted to focus at a point above the baseplate. At least two pins extend upwardly from the baseplate top surface and are fixed with respect to the foci of the mirrors. An accessory module has a flat bottomed positioning plate with portions defining pin holes to coincide with the pins of the face plate. A sample holding accessory platform extends from the positioning plate and is fixed with respect to the pin holes so that when the pin holes of the positioning plate are positioned over the pins of the baseplate and the positioning plate bottom surface is engaged with the locator pads on the baseplate, the sample is located at the foci of the mirrors. Three accessory module guides are located on the baseplate having spring-mounted retainer balls accurately spaced a common distance from the surface of the baseplate which engage beveled chamfers in the sides of the positioning plate and hold the accessory module in place. A sample to be analyzed may be placed in the accessory module and positioned in the FTIR spectrometer by hand, requiring no tools to accurately position the sample.

23 Claims, 4 Drawing Sheets

MODULAR OPTICAL SYSTEM FOR FOURIER TRANSFORM INFRARED SPECTROMETER

FIELD OF THE INVENTION

This invention relates generally to Fourier transform infrared spectrometers, and particularly to sample holding and mounting systems for such spectrometers.

BACKGROUND OF THE INVENTION

Fourier transform infrared (FTIR) spectrometers are utilized to provide accurate and efficient identification of the chemical composition of a sample. Such spectrometers typically incorporate a Michelson interferometer having a moving mirror. The interferometer modulates the infrared beam from an infrared source to provide an output beam in which the intensity of the infrared radiation at various wavelengths is periodically varied. The output beam is focused and passed through (or is reflected from) a sample, after which the beam is collected and focused onto a detector. The detector provides a time varying output signal which contains information concerning the wavelengths of infrared absorbence (or specular reflectance) of the sample. Fourier analysis is performed on the output signal data to yield usable information on the chemical composition of the sample.

With conventional FTIR instruments, the spectrometer is aligned during manufacture to provide optimum throughput based on published specifications. The overall height and geometry of the system optics generally define the height and lateral position of the focus, which is not normally specified, within the sample compartment at which the sample should be located. However, because of variations within the system optics the actual position of the focus can vary by a significant amount (in terms of tenths of millimeters) from the nominal position of the focus. This does not cause any significant problem for traditional large aperture transmission-based sampling accessories, such as cells or cuvettes. It does, however, cause a major problem for micro-sampling, and for the use of any specialized optical accessory.

Recently, the applications of modern FTIR instruments have been expanded by the use of special sampling accessories that involve precise beam imaging. The precision required by such accessories is at least an order of magnitude better than that provided by the beam imaging of a modern spectrometer. To accomodate modern accessories in modern instruments, accessory manufacturers provide a large degree of adjustment on many of the critical optical components within the accessory. This enables a given accessory to be custom aligned to specific instruments. For many modern accessories this is often a difficult and time-consuming exercise, and it is frequently too complex for an inexperienced operator. Once an accessory is removed from an instrument there is the danger that the precise alignment will be lost. Also, if the accessory is placed in another instrument of the same model a complete realignment of the accessory is usually required Without the customized alignment procedure, an accessory will either operate inefficiently, or in many cases will not operate at all. An ideal situation would be for an accessory manufacturer to provide pre-aligned accessories. However, the optical path variations of most current instruments is too great to make this practical, thus requiring a procedure of accessory alignment on these instruments.

SUMMARY OF THE INVENTION

The present invention comprises a modular optical system for a Fourier transform infrared spectrometer which has a baseplate assembly with a substantially flat baseplate and two mirrors fixed to the baseplate to focus at a point above the baseplate. At least two and preferably three register pins extend upwardly from the baseplate and are fixed with respect to the focus of the mirrors. Three spaced locator pads are also mounted to the baseplate and preferably have spherical top surfaces. In a preferred form at least two and preferably three accessory module guides are mounted on the baseplate to locate and position an accessory module. Each guide has a beveled top face, a vertical face, and a spring-loaded retainer ball protruding from the vertical face of the guide. The spring-loaded retainer ball of each guide is adapted to releaseably engage the chamfered edge of an accessory module positioning plate. An accessory module has a positioning plate with a substantially flat bottom surface and at least two pin holes is positioned to fit over the register pins of the baseplate. The top surfaces of the locator pads engage the flat bottom surface of the positioning plate to define, with the three points of contact, the plane in which the positioning plate is to be located. A sample holding accessory extends from the positioning plate and is fixed with respect to the pin holes such that when the pin holes are positioned over the pins, the sample platform will be located at the foci of the mirrors. The accessory module may have a mount plate extending vertically from the base and having portions defining a beam aperture. The guides and pins of the baseplate assembly are so arranged that the accessory module may be accurately positioned on the baseplate assembly by simple hand pressure and without the need for tools. Once installed, the accessory module is held firmly in position by the spring loaded retainers of the guides, but it may also be removed easily when desired. Accessory modules of differing configurations may be substituted one for the other without necessitating a readjustment of the focus of the mirrors or the FTIR spectrometer.

The modular optical system of the present invention permits rapid sample positioning and removal as well as the quick substitution of one type of sample holder for another. Because the base plate locator pads, the register pins and the guides cooperate to precisely position the accessory holder in three dimensions, accessory holders may be properly adjusted by the manufacturer so that the user of the spectrometer need not be skilled in spectrometer adjustment.

Further objects, features, and advantages of the invention will be apparent from the following detailed description when taken in conjunction with the accompanying drawings.

DESCRIPTION OF THE PREFERRED EMBODIMENT

Figure 1:
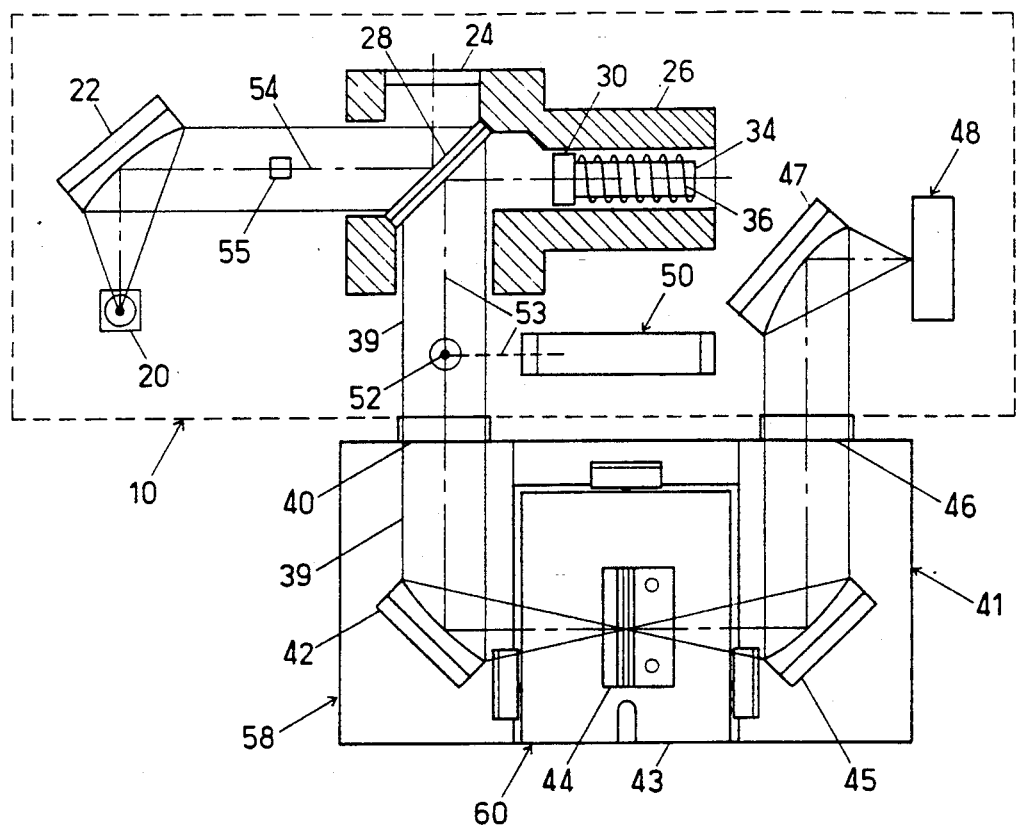
FIG. 1 is a schematic view of the modular optical system of the invention installed in a FTIR spectrometer.

The optical layout of a representative FTIR spectrometer system utilizing a Michelson interferometer is illustrated generally in schematic form at 10 in FIG. 1. Interferometer systems may be laid out in many geometries; the one illustrated in FIG. 1 is intended to be exemplary of the many geometries possible for utilization of the modular optical system of the present invention. The radiation emanating from an infrared source 20 is reflected off of a collimating mirror 22 which directs the radiation in a beam toward a beam splitter 24, located in an interferometer housing 26. The infrared light which is reflected by the beam splitter 24 is then reflected by a reflecting mirror 28 back to the beam splitter. Part of this infrared light passes through the beam splitter along a straight path which passes through an infrared transmissive window 40 and extends to a focusing mirror 42. Infrared light from the source which passes through the beam splitter 24 reflects off the moving mirror 30 back to the beam splitter, and a portion of this light is reflected by the beam splitter toward the mirror 42 and, along with the infrared from the mirror 28 which passes through the beam splitter, forms a beam 39. Variations in the pathlength between the beam splitter 24 and the mirrors 28 and 30 as the mirror 30 is moved result in selective destructive and constructive interference of wavelengths of infrared in the beam 39.

The moving mirror 30 is mounted on a shaft 34 which is reciprocated on a linear axis forwardly and rearwardly by a coil 36. The driving and control of the moving mirror is conventional and may be accomplished in any suitable way, for example, as described in U.S. Pat. Nos. 4,799,001 and 4,847,878.

Infrared leaving the interferometer housing 26 in the beam 39 passes through the infrared transmissive window 40 into a modular optical system 41. The window 40 serves to seal off the optical system 41 from the interior of the spectrometer 10 so that gases within the enclosure (not shown) for the optical system 41 do not pass into the spectrometer 10, and vice versa. After passing through the window 40, the beam 39 is reflected by the parabolic focusing mirror 42 through a sample chamber 43 containing a sample holding accessory 44. After passing through the sample held in the holder 44, the beam is reflected by a parabolic mirror 45 through an output window 46 to a focusing mirror 47 which focuses the beam on a detector 48. The signal from the detector 48 can be analyzed in a manner conventional in Fourier transform infrared spectrometers to characterize the substance contained in the sample holding accessory 44.

For appropriate and accurate frequency domain information to be generated by the FTIR spectrometer system, the direction of motion, the speed of motion, and the position of the moving mirror 30 must be controlled at all times. For this purpose, a laser interferometer system may be is used to precisely indicate motion and position of the moving mirror 30. This system consists of a laser 50, the output beam of which is partially reflected by a small beam splitter 52 to follow a path parallel to the center of the infrared light path into the interferometer housing 26. The laser beam, indicated by the dashed lines labeled 53 in FIG. 1, is also split by the interferometer beam splitter 24, creating an output laser beam 54 with an output intensity varying sinusoidally with the motion of the mirror 30 due to constructive and destructive interference in the interferometer. The output beam 54 is detected by a detector 55 which puts out an electrical signal corresponding to the intensity of the light received by it. As the mirror 30 moves, the intensity of the output beam 54 varies in a sine function, as detected at the detector 55, with each cycle representing a fixed increment of linear movement of the moving mirror. The sinusoidally varying signal produced by the detector 54 may be digitized by a zero-crossing detection circuit (not shown) which generates a pulsed output. See, e.g., U.S. Pat. No. 4,847,878 for exemplary detection circuitry.

Figure 2:
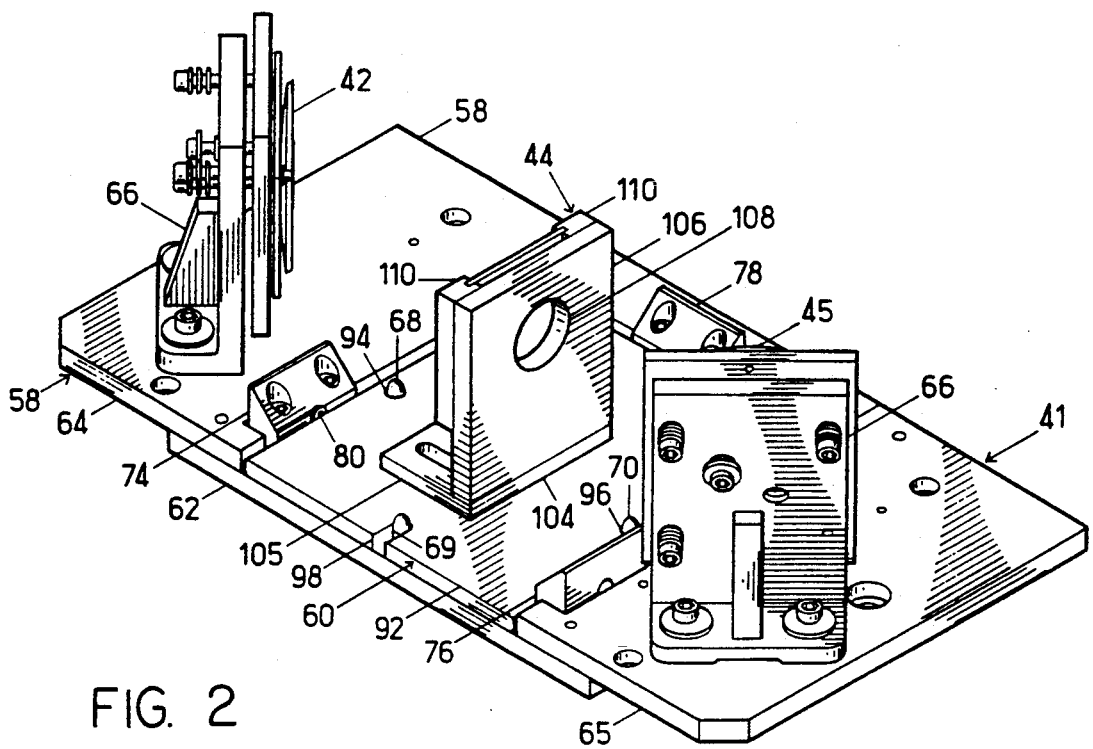
FIG. 2 is an isometric view of the modular optical system of this invention, showing an accessory module mounted to the baseplate assembly.

As best illustrated in FIG. 2, the modular optical system 41 includes a baseplate assembly 58 and an accessory module 60. The baseplate assembly 58, as shown separately in FIGS. 3 and 4, has a baseplate 62 with a flat top surface 63. A left mirror plate 64 and a right mirror plate 65 are mounted to the baseplate 62, although they may be integrally formed with the baseplate. The mirror plates 64, 65 are rigidly attached to the baseplate 62 and serve as bases for the mounting of the mirror supports 66 to which the focusing mirrors 42 and 45 are attached.

Positioning register pins 68, 69 and 70 are rigidly fixed to the baseplate 62. At least two pins are required but there are preferably three pins which extend upwardly from the baseplate top surface. A left pin 68 is spaced inwardly from the edge of the left mirror plate 64. Across from the left pin 68 a right pin 70 is spaced inwardly from the right mirror plate 65. A front pin 69 is spaced inwardly from the front of the baseplate 62.

Figure 3:
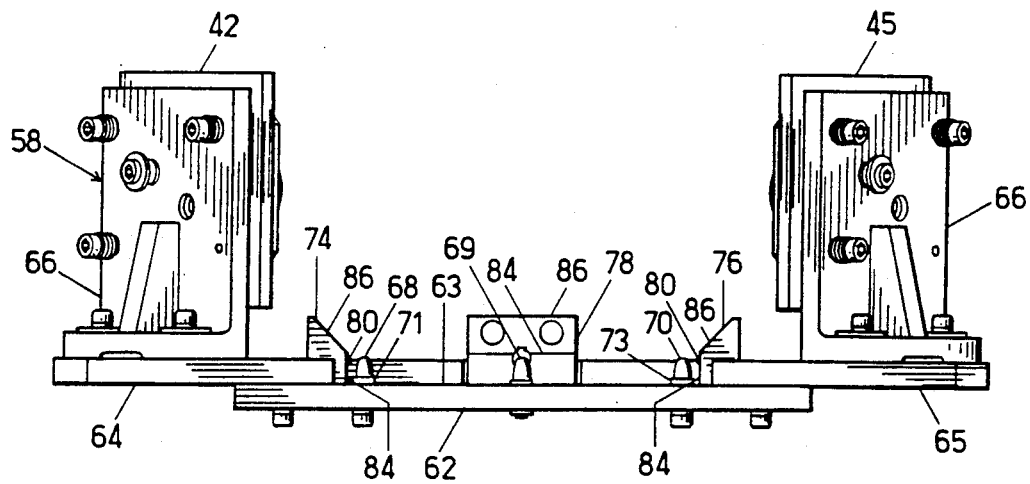
FIG. 3 is a front elevational view of the baseplate assembly of the modular optical system of FIG. 2.
Figure 4:
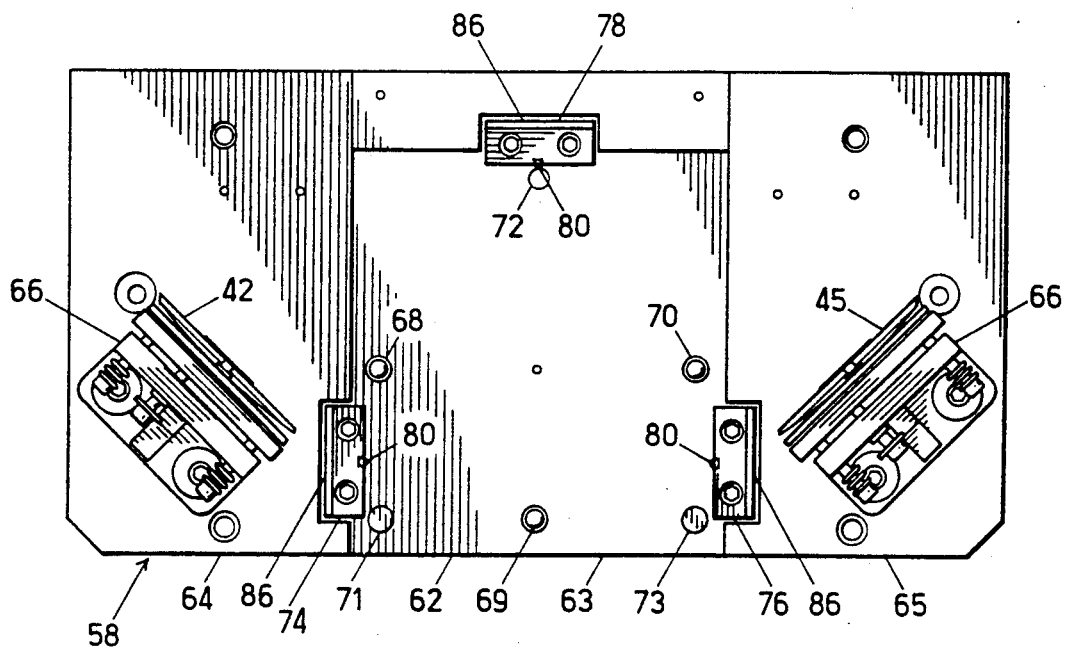
FIG. 4 is a top plan view of the baseplate assembly of FIG. 2.

Three locator pads 71, 72 and 73 are mounted to the baseplate and each preferably has a rounded or spherical top surface which extends above the surface of the baseplate, as illustrated in FIG. 3 (the pad 72 is hidden by the pin 69 in FIG. 3). The pads are preferably spaced from one another about the baseplate, preferably as shown in FIG. 4 wherein the pad 72 is on the opposite side of the baseplate from the center pin 69 and the pads 71 and 73 are at the far corners of the baseplate from the pad 72. The tops of each pad preferably are at the same height and define a desired plane for fixing the position of the accessory module.

Figure 7:
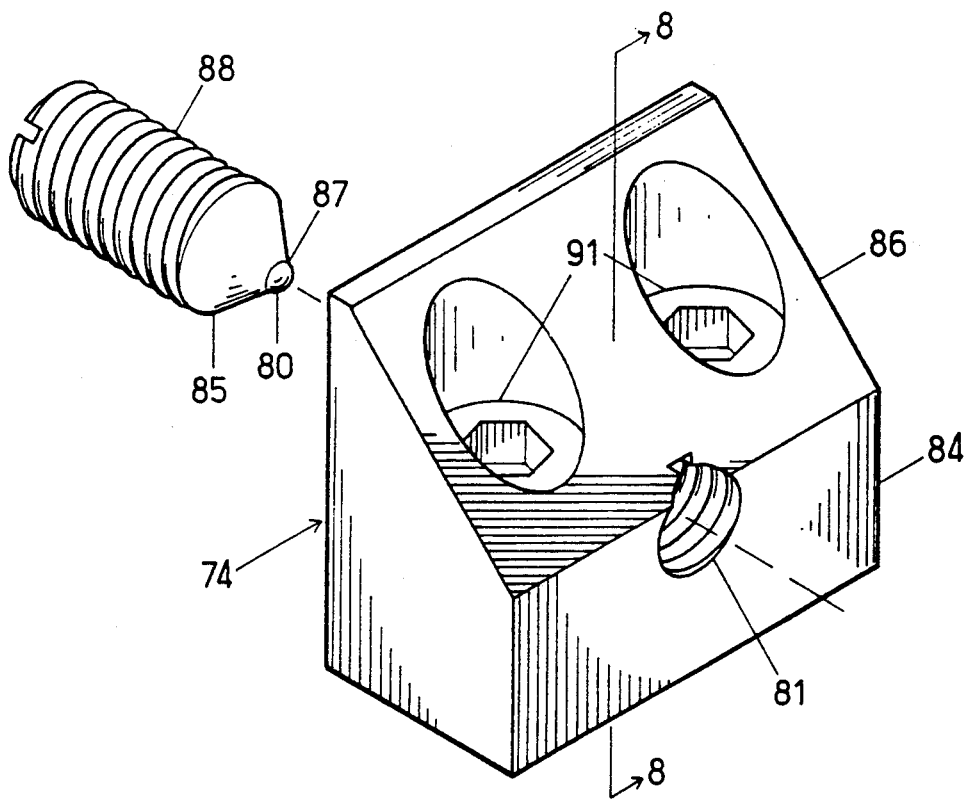
FIG. 7 is an enlarged exploded isometric view of an accessory module guide of the baseplate assembly of FIG. 2.
Figure 8:
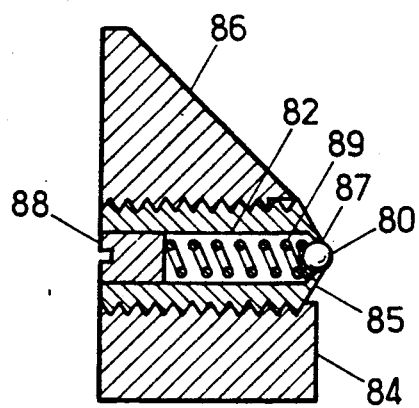
FIG. 8 is a cross-sectional view of an accessory module guide taken generally along the lines 8—8 of FIG. 7.

Three accessory module guides 74, 76, 78 are mounted on the baseplate 62. The left accessory module guide 74 is located outwardly and to the front of the left pin 68 and adjacent the left locator pad 71, and the right accessory module guide 76 is located across from the left accessory module guide 74 and is outwardly of the right pin 70 and adjacent the right locator pad 73. The rear accessory module guide 78 is located at the side of the baseplate opposite the front pin 72 and adjacent the rear locator pad 72. The left accessory module guide 74, which is identical to the other guides, is shown in a partial exploded view in FIG. 7. Each accessory module guide has a metallic block with an inclined top face 86 and a front face 84 which is substantially perpendicular to the baseplate 62. At an accurately spaced distance from the baseplate 62, a threaded screw hole 81 is formed which accepts a threaded screw body 88. A cylindrical cavity 82, as best shown in FIG. 8, is formed in the screw body 88. The cavity tapers inwardly in proximity to the front face 84 of the accessory module guide to form a lip 85 surrounding an opening 87. When inserted in the screw hole 81 the screw body 88 pierces both the front face 84 and the top face 86. A retainer ball 80, which may be formed of metal or any suitable plastic, but which is preferably formed of nylon, is spring-loaded by a spring 89 against the lip 85 of the opening 87 so that a desired portion of the ball 80 projects beyond the screw body 88 and the front face 84 of the accessory module guide. Screws 91 or other appropriate fasteners may be used to fix the accessory module guides to the baseplate 62.

Figure 5:
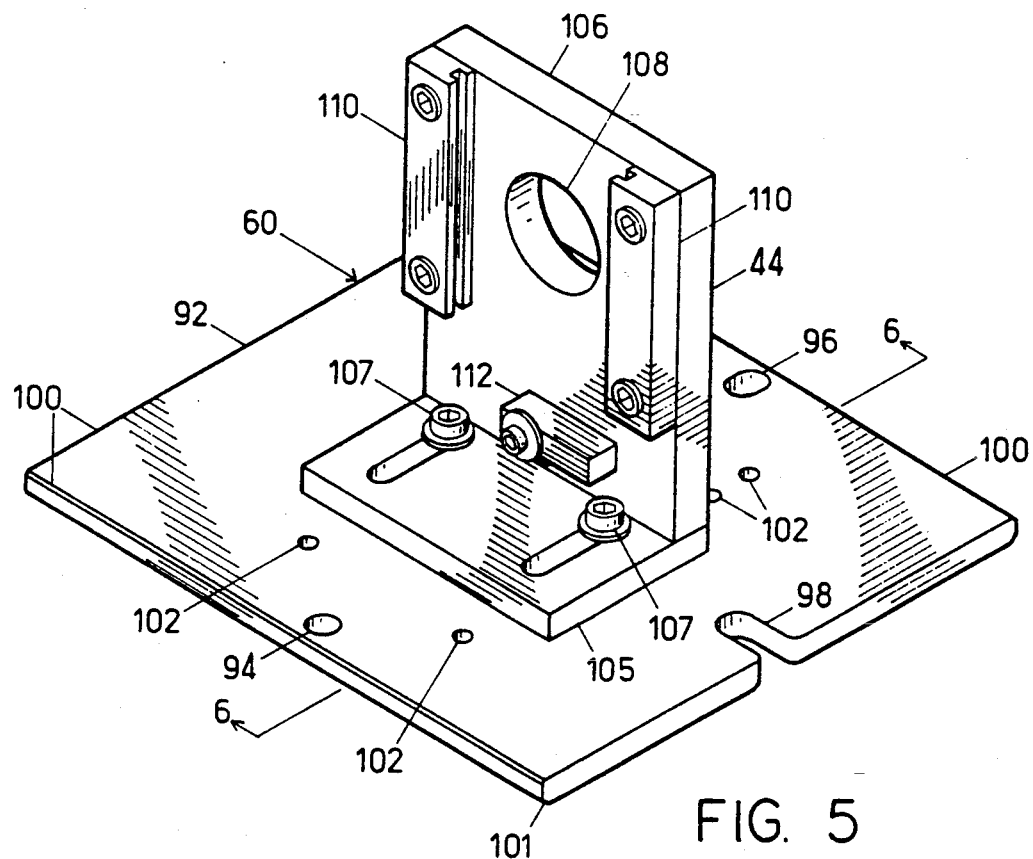
FIG. 5 is an isometric view of the accessory module of the modular optical system of FIG. 1.
Figure 6:
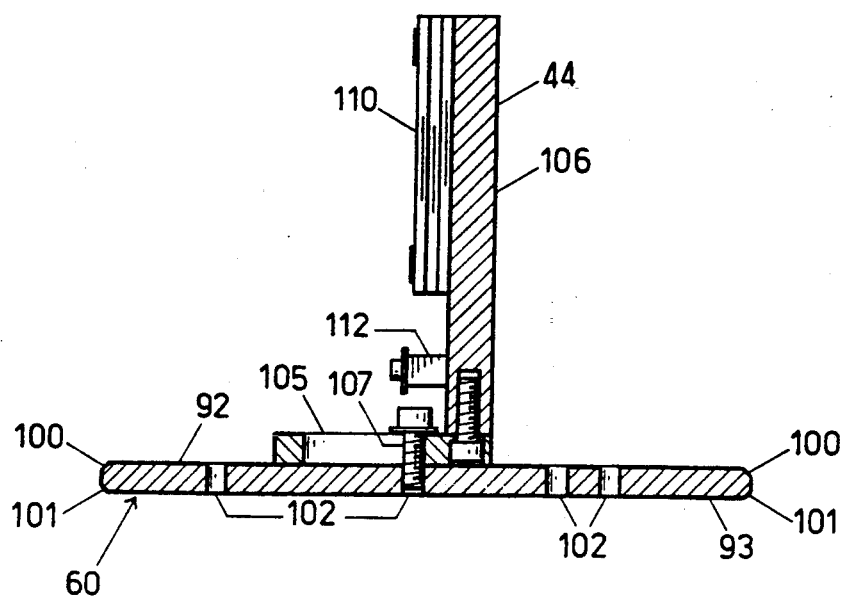
FIG. 6 is a cross-sectional view of the accessory module taken along section lines 6—6 of FIG. 5.

The accessory module 60, shown in FIGS. 2, 5 and 6, has a rectangular positioning plate 92 which is dimensioned to fit between the three accessory module guides 74, 76, and 78. The bottom surface 93 of the positioning plate 92 is also substantially flat so that the positioning plate 92, when resting on the baseplate 62, will be oriented in substantially the same plane as the top surface of the baseplate 62. The accuracy of the flatness of the bottom surface of the positioning plate will be determined by the acceptable tolerance in vertical positioning of the accessory module 60 on the baseplate 62. For each register pin located on the baseplate 62, a pin hole is provided in the positioning plate 92. A circular pin hole 94 is provided to admit the left pin 68; an oval pin hole 96 is provided to admit the right pin 70; and a pin notch 98 is provided to admit the front pin 69. Beveled top chamfers or bezels 100 are provided on the left, right, and rear faces of the positioning plate 92 so as to be adjacent the accessory module positioning guides. Beveled bottom chamfers 101 are also provided on those faces to act to depress the retainer balls 80 when the accessory module 60 is pressed into place on the baseplate assembly 58.

A variety of bolt holes 102 may be provided in the positioning plate 92 to permit the attachment of any desired sample holding accessory. One such accessory is the sample holder 44 shown in FIGS. 2, 5 and 6. The sample holder 44 has a mount plate 106 which extends vertically upward from a sample holder baseplate 105 which is positionably attached to the positioning plate 92 by bolts 107. The mount plate 106 has a generally circular beam aperture 108. Two vertical grooved members 110 together with a sample stop 112 provide a sample platform for holding a sample to be analysed in front of the beam aperture 108.

When it is desired to analyze a sample in an FTIR spectrometer equipped with the modular optical system of this invention, the sample is secured in place on the sample holder 44 on the accessory module 60. To obtain a proper analysis of the sample, the sample must be precisely positioned at the foci of the two focusing mirrors 42 and 45. The mirrors 42 and 45 generally will have been pre-adjusted at the factory or by a skilled technician to focus at a spot in precise relation to the three positioning pins 68, 69 and 70 and the locator pads 71, 72 and 73. The sample holder 44 will also have been precisely located on the positioning plate 92 so that, when the positioning plate is mounted to the base assembly, the sample will be in a precise desired position with respect to the focusing mirrors.

To correctly position the sample in the sample holder 44 the accessory module 60 is first positioned by an operator so that the pin holes 94, 96 overlie the register pins 68 and 70 respectively. The pin notch 98 will then overlie the front pin 69. The accessory module 60 will then be properly positioned over the baseplate 62 and will be supported on the retainer balls 80 of the three accessory module guides 74, 76, 78. A gentle but firm hand pressure applied by the operator to the accessory module 60 will cause the bottom bezels 101 of the positioning plate 92 to push the retainer balls 80 into the cylindrical cavities 82 of the accessory module guides, allowing the bottom of the positioning plate 92 to come into contact (i.e., substantially point contact) with the tops of the locator pads 71, 72 and 73. The three register pins 68, 69, and 70, when engaged in the holes in the positioning plate, accurately locate the accessory module 60 laterally, longitudinally and rotationally (about an axis normal to the baseplate) with respect to the baseplate assembly, and the engagement of the bottom surface 93 of the positioning plate with the top surfaces of the locator pads 71, 72 and 73 locates the module 60 in a desired horizontal plane, having the position of the accessory module in elevation and about orthogonal axis which lie in the plane of the positioning plate. The retainer balls 80 of the accessory module guides engage the top chamfers 100 when the positioning plate 92 is correctly positioned vertically to provide a downward and inward force on the positioning plate. The accessory module guides 74, 76, 78 will act to snuggly retain the accessory module 60 in precise alignment with the mirrors 32, 44. No tools are required to insert the accessory module 60 into the baseplate assembly 58.

The modular optical system of the invention will accommodate accessory modules with any type of sample positioning means, for example, rotary slide sample holders, liquid sample holders, belt-fed sample holders, and others.

It is to be understood that the present invention is not limited to the particular embodiment disclosed herein, but embraces all such modified forms thereof as come within the scope of the following claims.

What is claimed is:

1. A modular optical system for a Fourier transform infrared spectrometer comprising:
   (a) a baseplate assembly having a baseplate with a top surface and two mirrors mounted to the baseplate to focus at a position above the baseplate, and including at least two register pins extending upwardly from the top surface of the baseplate which are fixed with respect to the foci of the mirrors;
   (b) an accessory module having a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position laterally, longitudinally, and rotationally with respect to the foci of the mirrors, and means for releasably clamping the positioning plate to the baseplate.

2. A modular optical system for a Fourier transform infrared spectrometer comprising:

(a) a baseplate assembly having a baseplate with a top surface and two mirrors mounted to the baseplate to focus at a position above the baseplate, and including at least two register pins extending upwardly from the top surface of the baseplate which are fixed with respect to the foci of the mirrors;

(b) an accessory module having a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position laterally, longitudinally, and rotationally with respect to the foci of the mirrors;

including three located pads with rounded tops, the pads mounted on the baseplate to engage the bottom surface of the positioning plate to locate precisely the accessory module in elevation and in rotation about an axis in the plane of the positioning plate.

3. A modular optical system for a Fourier transform infrared spectrometer comprising:

(a) a baseplate assembly having a baseplate with a top surface and two mirrors mounted to the baseplate to focus at a position above the baseplate, and including at least two register pins extending upwardly from the top surface of the baseplate which are fixed with respect to the foci of the mirrors;

(b) an accessory module having a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position laterally, longitudinally, and rotationally with respect to the foci of the mirrors;

further including accessory module guides rigidly attached to the baseplate and spaced from the focus of the mirrors and having spring-loaded retainer balls adapted to engage the positioning plate of the accessory module and cooperating with the baseplate to vertically position the accessory module.

4. The modular optical system of claim 3 wherein the positioning plate has four sides and beveled chamfers located along at least two sides of the positioning plate, the chamfers being adapted to be engaged by the retainer balls of the accessory module guides to restrict vertical motion and aid the horizontal stability of the positioning plate.

5. An accessory module for a Fourier transform infrared spectrometer modular optical system comprising:

(a) a positioning plate having front, back, left and right sides and a substantially flat bottom surface, a first pin hole therein spaced inwardly from the left side; a second pin hole therein spaced inwardly from the right side; and a pin notch opening therein on the front side; and portions defining beveled chamfers on the top surface of the positioning plate along the left, right and back sides; and (b) means for attaching a sample holding accessory to the positioning plate.

6. The accessory module of claim 5 wherein the first pin hole is circular and the second pin hole is oblong in shape.

7. The accessory module of claim 5 further including a sample holding accessory attached to the positioning plate by the means for attaching the sample holding accessory and including a mount extending upwardly from the positioning plate and having portions defining a beam aperture, and means on the mount for holding a sample to be analyzed in front of the beam aperture.

8. A baseplate assembly for a Fourier transform infrared spectrometer modular optical system, comprising:

(a) a baseplate having a substantially flat top surface;
(b) two mirrors with a common focus mounted on the baseplate;
(c) at least two pins mounted on the top surface of the baseplate between the mirrors;
(d) at least three accessory module guides having spring-loaded retainer balls accurately spaced a common distance from the surface of the baseplate.

9. The baseplate assembly of claim 8 including three locator pads with rounded tops, the pads mounted on the baseplate at spaced positions so that the tops of the pads define a plane.

10. A modular optical system for a Fourier transform infrared spectrometer comprising:

(a) a baseplate having a flat top surface;
(b) two mirrors mounted on the baseplate with a common focus above the baseplate;
(c) three register pins extending upwardly from the baseplate top surface and spaced a fixed distance from the edges of the baseplate;
(d) a positioning plate having portions defining a circular pin hole, an oval pin hole and a pin notch which spaced and adapted to receive the pins of the baseplates so as to fix the positioning plate with respect to the baseplate;
(e) a sample holding accessory mounted to and extending vertically upwardly from the positioning plate and having portions defining a beam aperture, wherein when the positioning plate is fitted onto the baseplate the beam aperture is located at the foci of the mirror; and
(f) accessory module positioning guide means attached to the baseplate in position for releasably clamping the positioning plate to the baseplate.

11. The system of claim 10 including three locator pads with rounded tops, the pads mounted to the baseplate at spaced positions to engage the bottom of the positioning plate and support it in a desired plane.

12. A Fourier transform infrared spectrometer system comprising:

(a) a source of infrared radiation which provides a beam of infrared;
(b) an interferometer which receives the beam from the source and produces a modulated output beam;
(c) an infrared detector;
(d) focusing optics for focusing a received beam onto the detector;
(e) a modulator optical system which receives the beam from the interferometer and provides a beam to the focusing optics, comprising:
a baseplate assembly mounted in a fixed position with respect to the interferometer and the focusing optics and including, a first mirror receiving the beam from the interferometer and directing the beam to a selected position and a second mirror receiving the beam from the selected position and directing it to the focusing optics, an accessory module having means thereon for mounting a sample holding accessory, means on the baseplate assembly and accessory module for detachably mounting the accessory module to the baseplate assembly such that a sample holding accessory will be in a predetermined position with respect to the first and second mirrors so that the infrared beam from the first mirror passes to or is reflected from the sample and is received from the second mirror, wherein the baseplate assembly includes a baseplate with a top surface and wherein the two reflecting mirrors are mounted to the baseplate to focus at a position above the baseplate, and including at least two register pins extending upwardly from the top surface of the baseplate which are fixed with respect to the foci of the mirrors, and wherein the accessory module has a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position with respect to the foci of the mirrors, and means for releasably clamping the positioning plate to the baseplate.

13. The spectrometer system of claim 12 wherein the baseplate has three register pins extending upwardly from the top surface of the baseplate at spaced positions and the accessory module positioning plate has three pin holes positioned to receive the register pins of the baseplate.

14. The spectrometer system of claim 12 further including a sample holding accessory attached to the positioning plate by the means for attaching the sample holding accessory and including a mount extending upwardly from the positioning plate and having portions defining a beam aperture, and means on the mount for holding a sample to be analyzed in front of the beam aperture.

15. A Fourier transform infrared spectrometer system comprising:

(a) a source of infrared radiation which provides a beam of infrared;

(b) an interferometer which receives the beam from the source and produces a modulated output beam;

(c) an infrared detector;

(d) focusing optics for focusing a received beam onto the detector;

(e) a modular optical system which receives the beam from the interferometer and provides a beam to the focusing optics, comprising:

a baseplate assembly mounted in a fixed position with respect to the interferometer and the focusing optics and including, a first mirror receiving the beam from the interferometer and directing the beam to a selected position and a second mirror receiving the beam from the selected position and directing it to the focusing optics, an accessory module having means thereon for mounting a sample holding accessory, means on the baseplate assembly and accessory module for detachably mounting the accessory module to the baseplate assembly such that a sample holding accessory will be in a predetermined position with respect to the first and second mirrors so that the infrared beam from the first mirror passes to or is reflected from the sample and is received from the second mirror, wherein the baseplate assembly includes a baseplate with a top surface and wherein the two reflecting mirrors are mounted to the baseplate to focus at a position above the baseplate, and including at least two register pins extending upwardly from the top surface of the baseplate which are fixed with respect to the foci of the mirrors.

and wherein the accessory module has a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position with respect to the foci of the mirrors, including three locator pads with rounded tops, the pads mounted to the baseplate at spaced positions to engage the bottom of the positioning plate to support it in a desired plane.

16. A Fourier transform infrared spectrometer system comprising:

(a) a source of infrared radiation which provides a beam of infrared;

(b) an interferometer which receives the beam from the source and produces a modulated output beam;

(c) an infrared detector;

(d) focusing optics for focusing a received beam onto the detector;

(e) a modulator optical system which receives the beam from the interferometer and provides a beam to the focusing optics, comprising:

a baseplate assembly mounted in a fixed position with respect to the interferometer and the focusing optics and including, a first mirror receiving the beam from the interferometer and directing the beam to a selected position and a second mirror receiving the beam from the selected position and directing it to the focusing optics, an accessory module having means thereon for mounting a sample holding accessory, means on the baseplate assembly and accessory module for detachably mounting the accessory module to the baseplate assembly such that a sample holding accessory will be in a predetermined position with respect to the first and second mirrors so that the infrared beam from the first mirror passes to or is reflected from the sample and is received from the second mirror, wherein the baseplate assembly includes a baseplate with a top surface and wherein the two reflecting mirrors are mounted to the baseplate to focus at a position above the baseplate, and including at least two register pins extending upwardly from the top surface of the baseplate which are fixed with respect to the foci of the mirrors, and wherein the accessory module has a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position with respect to the foci of the mirrors, wherein the means for detechably mounting the accessory module to the baseplate assembly further includes accessory module guides rigidly attached to the baseplate and spaced from the focus of the mirrors and having spring loaded retainer balls adapted to engage the positioning plate of the accessory module and cooperating with the baseplate to vertically position the accessory module.

17. The spectrometer system of claim 16 wherein the positioning plate has four sides and beveled chamfers located along at least two sides of the positioning plate, chamfers being adapted to be engaged by the retainer balls of the accessory module guides to restrict the motion of the positioning plate.

18. A Fourier transform infrared spectrometer system comprising:
(a) a source of infrared radiation which provides a beam of infrared;
(b) an interferometer which receives the beam from the source and produces a modulated output beam;
(c) an infrared detector;
(d) focusing optics for focusing a received beam onto the detector;
(e) a modular optical system which receives the beam from the interferometer and provides a beam to the focusing optics, comprising:
a baseplate assembly mounted in a fixed position with respect to the interferometer and the focusing optics and including,
a first mirror receiving the beam from the interferometer and directing the beam to a selected position and a second mirror receiving the beam from the selected position and directing it to the focusing optics,
an accessory module having means thereon for mounting a sample holding accessory,
means on the baseplate assembly and accessory module for detachably mounting the accessory module to the baseplate assembly such that a sample holding accessory will be in a predetermined position with respect to the first and second mirrors so that the infrared beam from the first mirror passes to or is reflected from the sample and is received from the second mirror,
wherein the baseplate assembly includes a baseplate with a top surface and wherein the two reflecting mirrors are mounted to the baseplate to focus at a position above the baseplate, and including at least two register pins extending upwardly from the top surface of the baseplate which are fixed with respect to the foci of the mirrors, and wherein the accessory module has a positioning plate with a substantially flat bottom surface adapted to be supported by the baseplate, at least two pin holes in the positioning plate positioned to receive the register pins of the baseplate, and adapted to mount a sample holding accessory in a desired position, wherein the sample holding accessory will be fixed with respect to the pin holes such that when the pin holes receive the pins a sample holding accessory may be located at a desired position with respect to the foci of the mirrors, wherein a first pin hole in the positioning plate is circular and a second pin hole is oblong in shape.

19. A modular optical system for a Fourier transform infrared spectrometer comprising:
(a) a baseplate assembly having a baseplate with a top surface and two mirrors mounted to the baseplate to focus at a position above the baseplate, and including three locator pads with rounded tops mounted to the baseplate;
(b) an accessory module having a positioning plate with a substantially flat bottom surface adapted to engage with the top surfaces of the locator pads, and adapted to mount a sample holding accessory in a desired position, wherein the sample holding accessory will be fixed in a plane when the positioning plate is supported on the locator pads; and
(c) accessory module positioning guide means attached to the baseplate in position for releasably clamping the positioning plate to the baseplate.

20. The modular optical system of claim 19 wherein the guide means comprise accessory module guides rigidly attached to the baseplate and spaced from the focus of the mirrors and having spring-loaded retainer balls adapted to engage the positioning plate of the accessory module and cooperating with the baseplate to vertically position the accessory module.

21. The modular optical system of claim 20 wherein the positioning plate has four sides and beveled chamfers located along at least two sides of the positioning plate, the chamfers being adapted to be engaged by the retainer balls of the accessory module guides to restrict vertical motion and aid the horizontal stability of the positioning plate.

22. The modular optical system of claim 19 wherein the baseplate has at least two register pins extending upwardly from its top surface and the positioning plate has at least two pin holes positioned to received the pins.

23. A baseplate assembly for a Fourier transform infrared spectrometer modular optical system, comprising:
(a) a baseplate having a substantially flat top surface;
(b) two mirrors with a common focus mounted on the baseplate;
(c) three rounded top locator pads mounted to the baseplate on the top surface between the mirrors;
(d) at least three accessory module guides mounted to the baseplate having spring-loaded retainer balls accurately spaced a common distance from the surface of the baseplate.

* * * * *

UNITED STATES PATENT AND TRADEMARK OFFICE
CERTIFICATE OF CORRECTION

PATENT NO. : 5,153,675
DATED : October 6, 1992
INVENTOR(S) : Kenn A. Beauchaine

It is certified that error appears in the above-identified patent and that said Letters Patent is hereby corrected as shown below:

Column 1, line 62, change "required" to --required.--.

Column 7, line 19, change "located" to --locator--.

Column 8, line 63, change "modulator' to --modular--.

Signed and Sealed this

Fifth Day of October, 1993

Attest:

BRUCE LEHMAN

Attesting Officer     Commissioner of Patents and Trademarks